(12) United States Patent
Freyman et al.

(10) Patent No.: US 8,740,844 B2
(45) Date of Patent: Jun. 3, 2014

(54) MEDICAL DEVICE WITH DRUG DELIVERY MEMBER

(75) Inventors: Toby Freyman, Watertown, MA (US); Timothy J. Mickley, Elk River, MN (US); Maria J. Palasis, Wellesley, MA (US); Wendy Naimark, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1325 days.

(21) Appl. No.: 10/645,653

(22) Filed: Aug. 20, 2003

(65) Prior Publication Data

US 2005/0043678 A1 Feb. 24, 2005

(51) Int. Cl.
*A61M 31/00* (2006.01)
*A61M 29/02* (2006.01)

(52) U.S. Cl.
CPC ..................................... *A61M 29/02* (2013.01)
USPC .................................................. 604/103.01

(58) Field of Classification Search
USPC ....................... 604/103, 103.1, 103.2, 103.01
See application file for complete search history.

(56) References Cited

U.S. PATENT DOCUMENTS

| | | | |
|---|---|---|---|
| 5,395,309 A * | 3/1995 | Tanaka et al. .................... | 604/18 |
| 5,637,086 A | 6/1997 | Ferguson et al. | |
| 5,713,853 A * | 2/1998 | Clark et al. .................... | 604/509 |
| 5,868,719 A | 2/1999 | Tsukemik | |
| 6,010,480 A | 1/2000 | Abele et al. | |
| 6,050,930 A | 4/2000 | Teirstein | |
| 6,123,697 A * | 9/2000 | Shippert ....................... | 604/514 |
| 6,350,253 B1 | 2/2002 | Deniega et al. | |
| 6,364,856 B1 * | 4/2002 | Ding et al. ............... | 604/103.02 |
| 6,364,900 B1 * | 4/2002 | Heuser ......................... | 623/1.11 |
| 6,398,758 B1 | 6/2002 | Jacobsen | |
| 6,425,853 B1 | 7/2002 | Edwards | |
| 6,440,097 B1 | 8/2002 | Kupiecki | |
| 7,241,273 B2 * | 7/2007 | Maguire et al. .............. | 604/6.16 |
| 7,563,247 B2 * | 7/2009 | Maguire et al. ............... | 604/104 |
| 2005/0043678 A1 * | 2/2005 | Freyman et al. ......... | 604/103.01 |
| 2005/0171563 A1 * | 8/2005 | Heinrich et al. .............. | 606/153 |

* cited by examiner

*Primary Examiner* — Nicholas Lucchesi
*Assistant Examiner* — Diva K Chander
(74) *Attorney, Agent, or Firm* — Vidas, Arrett & Steinkraus

(57) ABSTRACT

The present invention generally relates to a medical device for delivering a therapeutic agent to an internal portion of a patient's body. The medical device includes a shaft and a self-expanding delivery member in operative communication with the shaft. The delivery member is shaped from a porous material that is capable of releasing a therapeutic agent to an internal portion of a patient's body. The medical device further includes a therapeutic agent delivery lumen in fluid communication with the delivery member to fluidly connect the delivery member with a therapeutic agent source. A retention member may also be provided to selectively collapse the delivery member.

16 Claims, 7 Drawing Sheets

MEDICAL DEVICE WITH DRUG DELIVERY MEMBER

FIELD OF THE INVENTION

This invention relates generally to medical devices for delivering a therapeutic agent to an internal portion of a patient's body. More specifically, this invention is directed to medical devices having an expandable therapeutic agent delivery member capable of releasing a therapeutic agent to an internal portion of a patient's body.

BACKGROUND OF THE INVENTION

Various diseases may be treated by localized delivery of a therapeutic agent to an internal portion of a patient's body. For example, atherosclerotic disease, which is characterized by the build-up of plaque on the interior wall of an arterial vessel, may be treated by applying a therapeutic agent, such as heparin, to the diseased portion of a vessel wall. However, delivery and application of the therapeutic agent directly to the vessel wall may be complicated by the constant flow of blood through the vessel, which tends to carry the therapeutic agent downstream, away from the diseased tissue. Thus, a need exists for a device capable of effective localized delivery and application of a therapeutic agent to an internal portion of a patient's body, especially to the internal surface of a vessel or lumen.

Information relevant to attempts at addressing this or related needs can be found in such references as U.S. Pat. No. 5,868,719 to Tsukernik and U.S. Pat. No. 6,050,930 to Teirstein, each of which is incorporated by reference in its entirety herein. However, prior attempts at providing effective agent delivery devices suffer from certain disadvantages.

For example, prior devices may be limited in agent delivery capacity because they employ pre-loaded agent delivery members, such as partially or fully impregnated sponge bodies, to deliver a finite amount of agent to a body lumen. Such agent delivery members are impregnated with a therapeutic agent prior to a vessel treatment procedure and carry only a pre-determined amount of agent to a target region. Thus, a need exists for a device capable of delivering and applying a replenishable, active source of therapeutic agent to a body lumen.

In addition, prior devices may require the exertion of significant pressure upon a lumen wall, as with an inflatable member, to force a therapeutic agent from an agent delivery member impregnated with the therapeutic agent to the surface of a lumen wall. Thus, a need exists for a device capable of delivering and applying a therapeutic agent to the wall of a body lumen without the exertion of significant pressure upon the lumen wall.

A need further exists for a device capable of delivering and applying a therapeutic agent to a lumen wall in a controlled and uniform fashion. Moreover, a need exists for an agent delivery device designed to maximize the amount of agent actually applied to and absorbed by a lumen wall, while minimizing the amount of agent released from the device without being applied to or absorbed by the lumen wall. These and other objectives are accomplished by the present invention.

SUMMARY OF THE INVENTION

The present invention provides a medical device for delivering a therapeutic agent to an internal portion of a patient's body. In one embodiment, the medical device includes a shaft and a self-expanding delivery member in operative communication with the shaft. The delivery member may have a proximal end and a distal end and may be shaped in a generally solid cylindrical configuration from a porous material. The porous material may be capable of (i) releasing the therapeutic agent to an internal portion of a patient's body, and (ii) being held in a collapsed state. The medical device may further include a therapeutic agent delivery lumen defined by a lumen wall in which the lumen is in fluid communication with the delivery member to fluidly connect the delivery member with a therapeutic agent source. A retention member may also be provided. The retention member may be operatively connected with the delivery member and may be configured and arranged to selectively collapse the delivery member. The lumen wall may have one or more delivery openings therein for passage of the therapeutic agent therethrough. The delivery member may also be disposed around and in contact with at least a portion of the lumen wall and in contact with at least one of the delivery openings.

In another embodiment, the medical device includes a shaft and a self-expanding delivery member in operative communication with the shaft. The delivery member may have a proximal end and a distal end and may be shaped in a generally solid cylindrical configuration from a porous material. The porous material may be capable of (i) releasing the therapeutic agent to an internal portion of a patient's body, and (ii) being held in a collapsed state. The medical device may further include a therapeutic agent delivery lumen defined by a lumen wall in which the lumen is in fluid communication with the delivery member to fluidly connect the delivery member with a therapeutic agent source. A retention member may also be provided. The retention member may be operatively connected with the delivery member and may be configured and arranged to selectively collapse the delivery member. The delivery member, when in an expanded condition, may form a longitudinal conduit having an inner wall. The conduit may be disposed and arranged such that a body fluid may pass through the conduit while the delivery member is positioned within a patient's body. The delivery member may be selectively releasable from the medical device.

In another embodiment, the medical device includes a shaft and a self-expanding delivery member in operative communication with the shaft. The delivery member may have a proximal end and a distal end and may be shaped in a generally solid cylindrical configuration from a porous material. The porous material may be capable of (i) releasing the therapeutic agent to an internal portion of a patient's body, and (ii) being held in a collapsed state. The medical device may further include a therapeutic agent delivery lumen defined by a lumen wall in which the lumen is in fluid communication with the delivery member to fluidly connect the delivery member with a therapeutic agent source. A retention member may also be provided. The retention member may be operatively connected with the delivery member and may be configured and arranged to selectively collapse the delivery member. Negative pressure may be applied through therapeutic agent delivery lumen to remove fluid from the delivery member.

DESCRIPTION OF THE PREFERRED EMBODIMENTS

Exemplary medical devices embodying the principles of the present invention are shown throughout the drawings and will now be described in detail. In the following descriptions of various embodiments, similar elements or components thereof are designated with reference numbers having the same last two digits; redundant description is omitted.

Figure 1:
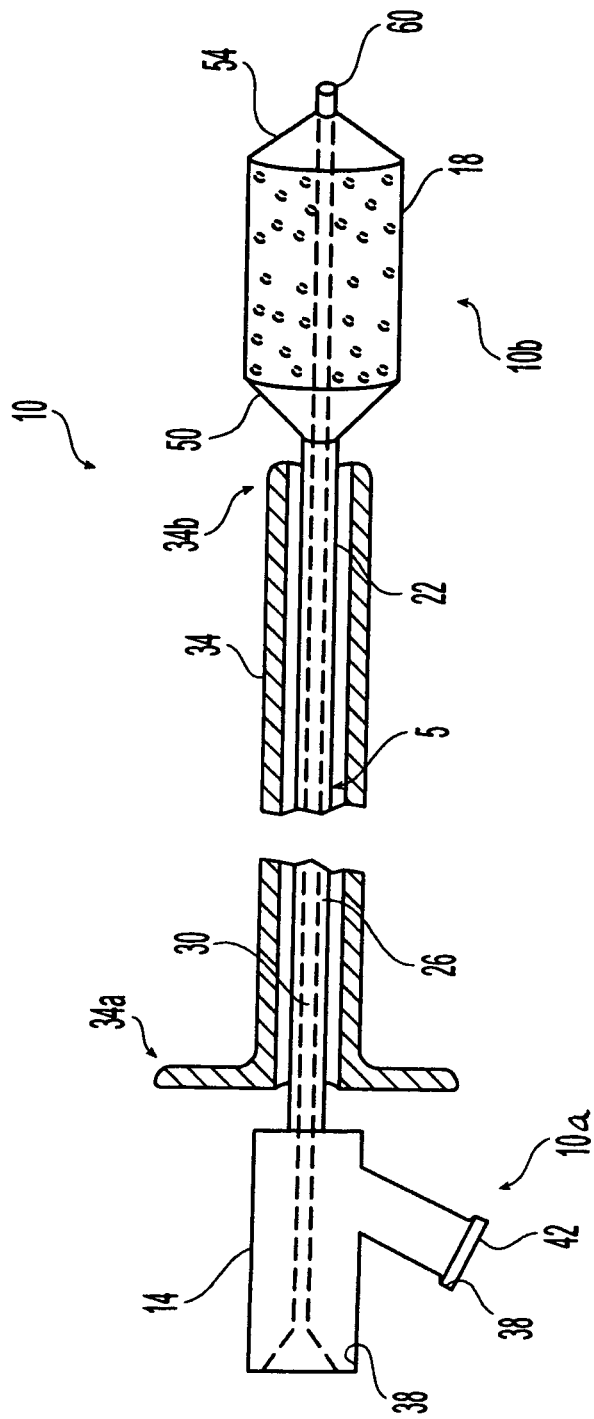
FIG. 1 is an elevational view, partially in cross-section, of a medical device formed in accordance with the present invention.
Figure 2:
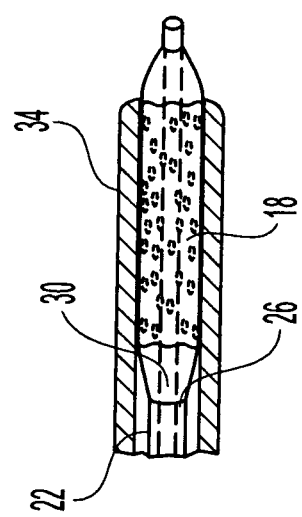
FIG. 2 is an elevational view, partially in cross-section, showing an agent delivery member formed in accordance with the present invention and being in a collapsed condition.

FIG. 1 illustrates a catheter-based embodiment of a medical device 10 in accordance with the present invention. Medical device 10 may have an agent supply manifold 14 at its proximal end 10a and a porous, self-expanding therapeutic agent delivery member 18 at its distal end 10b. Preferably, the agent delivery member 18 has a solid cylindrical shape. A longitudinal shaft 22 extends along the length of device 10 and carries a therapeutic agent delivery lumen 26, which fluidly connects manifold 14 with delivery member 18. The therapeutic agent delivery lumen 26 is defined by a lumen wall 5, which can be part of the shaft 22. The shaft 22 is in operative communication with the delivery member 18. Shaft 22 may also carry a wire lumen 30 for slidably receiving and tracking a steerable guide wire (not shown). A retention member 34, such as a sheath or longitudinal housing, may be slidably disposed about shaft 22 for selectively collapsing self-expanding delivery member 18 (as illustrated in FIG. 2).

Figure 3:
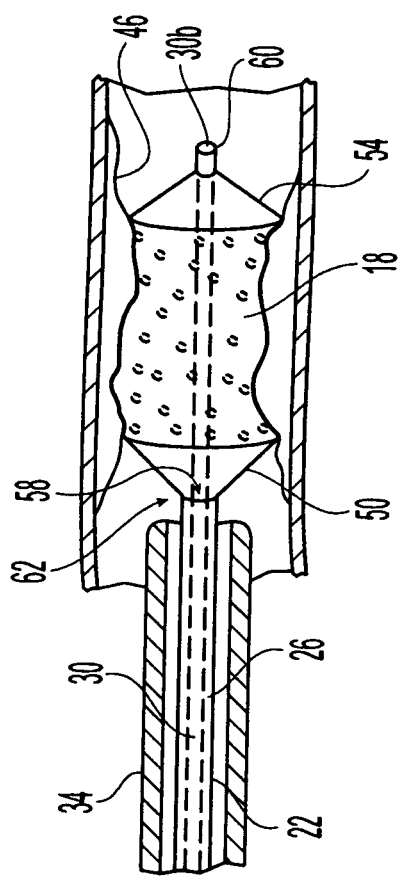
FIG. 3 is an elevational view, partially in cross-section, showing an agent delivery member formed in accordance with the present invention and being in an expanded condition inside a body lumen.

During operation of medical device 10, retention member 34 may be controlled by a user from proximal end 10a to maintain agent delivery member 18 in a collapsed condition (shown in FIG. 2) as agent delivery member 18 is positioned within a target treatment lumen. Thereafter, retention member 34 may be operated to release agent delivery member 18 from its collapsed condition, causing agent delivery member 18 to self-expand to a pre-determined diameter and bringing agent delivery member 18 into intimate contact with a target vessel wall 46. A therapeutic agent from a therapeutic agent source (not shown) may be delivered into agent delivery member 18 via agent delivery lumen 26 and subsequently released directly into target vessel wall 46 (as illustrated in FIG. 3). An application dwell time may be observed wherein agent delivery member 18 (and, therefore, the therapeutic agent) are held in fluid communication with the target vessel wall 46. Upon completion of the delivery and application of the therapeutic agent, excess agent may be removed from agent delivery member 18 by applying a negative pressure to agent delivery lumen 26. Thereafter, retention member 34 may be operated to collapse agent delivery member 18 for removal thereof from the target vessel region.

Manifold 14 may provide connection means 38, such as luer threads, for connecting device 10 to an active, replenishable therapeutic agent source. For example, manifold 14 may provide one or more agent delivery ports 42 connectable, via connection means 38, to a Luer syringe (not shown) filled with a therapeutic agent. Thus, a therapeutic agent may be delivered upon demand from the syringe through agent delivery port 42, manifold 14, and agent delivery lumen 26 into agent delivery member 18. Upon application of additional pressure, or upon delivery of additional agent, through agent delivery lumen 26, the therapeutic agent within agent delivery member 18 will be emitted from agent delivery member 18 into the target vessel. Moreover, the Luer syringe may be operated to apply a negative pressure to manifold 14 and agent delivery lumen 26 to draw excess agent away from agent delivery member 18 as desired.

Agent delivery member 18 may be shaped from an open-celled, porous, self-expanding material capable of both receiving a therapeutic agent from agent delivery lumen 26 and releasing the therapeutic agent on demand to an internal portion of a patient's body, such as into the wall of an arterial vessel or other body lumen. Such porous materials are capable of being compressed or being in a collapsed state. Suitable materials for forming agent delivery member 18 include, for example, carboxymethyl cellulose, polyacrylic acid, carboxymethyl starch, chitosan, potassium polymetaphosphates, polyethylene, nylon, polyurethane, PEBAX, silicone, alginate, cotton, and polymers cross-linked during phase transition. Other suitable materials also include collagen foams, PLA, PLGA, and PGA. Also, suitable porous materials may be degradable.

Agent delivery member 18 may be formed by a variety of manufacturing processes, such as by the introduction of gas bubbles into a liquid monomer or a melt, which is then solidified through polymerization, cross-linking, or cooling. In an exemplary manufacturing process, a melt of polypropylene is pressurized, and an inert gas, such as $CO_2$ or nitrogen, is introduced and forced into solution under high pressure. The pressure is then reduced, and the solubilized gas forms bubbles within the polymer causing a foamed condition. The foamed polymer is then solidified during a cooling process in which the polymer is cooled below its melting point. During cooling, cells within the polymer may form membranes separating the cells from other cells. These membranes may be ruptured via a reticulation process. The cooled foamed polymer may be cut, punched, or otherwise shaped to the desired specifications into agent delivery member 18. It should be appreciated that the polymer may, alternatively, be produced in a manner that results in an appropriately sized agent delivery member 1° (e.g., extrusion).

It should be appreciated that the pore size of the material from which agent delivery member 18 is shaped may be controlled during manufacture to produce a variety of delivery characteristics or to facilitate the delivery of different agents. For example, a smaller pore size may result in a more controlled flow rate of an agent into and out of the porous regions of delivery member 18. In one embodiment, appropriate pore sizes may range from 50 microns to 1 millimeter. In a preferred embodiment, appropriate pore sizes may range from 50 microns to 200 microns.

Agent delivery member 18 may be attached to or placed in operative communication with shaft 22, agent delivery lumen 26, or wire lumen 30, via an adhesive bond, thermal bond melting, by mechanical attachment (e.g., interlocking connectors), or by any other attaching means known in the art.

As illustrated in FIG. 3, agent delivery member 18 may be shaped to conform to, or at least contact, a portion of a body lumen 46 when agent delivery member 18 is released from retention member 34. For example, agent delivery member 18 may have, in its fully expanded condition, a generally solid cylindrical configuration with a predetermined cross-sectional diameter approximately the same or slightly larger (when unconstrained by body lumen 46) than the diameter of a target body lumen 46. Thus, upon delivery of agent delivery member 18 to a target area and release from retention housing 34, agent delivery member 18 may expand to gently conform to, or at least contact, the inner wall of body lumen 46. It should be appreciated that the agent delivery member 18 will conform to the shape of the target region. For example, agent delivery member 18 may be tapered to fit a tapering vessel geometry or conform to the internal contour of the target body lumen when the delivery member is in an expanded state.

In addition, the agent delivery member 18 is formed in a generally solid cylindrical configuration. Such a configuration provides several advantages. The solid configuration gives the agent delivery member 18 greater structural strength, preventing accidental tears in the agent delivery member 18. The solid cylindrical configuration also facilitates a more uniform delivery of a therapeutic agent. With a centrally located agent delivery lumen 26 (as described above and further below), a therapeutic agent delivered from agent delivery lumen 26 will permeate through the agent delivery member 18 at a uniform rate and reach all parts of the exterior of the agent delivery member 18 at the same time, where it is then delivered to the tissue to be treated.

The longitudinal length of agent delivery member 18 may be predetermined, for example, according to the therapeutic agent being delivered or the procedure being performed. When used to treat atherosclerotic disease, the longitudinal length of agent delivery member 18 may be, for example, in the range of from 5 mm to 40 mm according to the dimensions of the diseased arterial region to be treated. It should be appreciated that device 10 may be modified and configured to deliver and apply a therapeutic agent to many different types of vessels or lumina in a patient's body, each having its own shape and length requirements.

The porous character of delivery member 18 and its ability to self-expand to conform to the contour of body lumen 46 combine to facilitate more efficient delivery of a therapeutic agent to the inner wall of lumen 46. For example, the porous self-expanding material of delivery member 18 may facilitate an effective, yet sensitive, seal with the rough topography of a plaque-containing or stented artery such that a therapeutic agent may be directly released into or held in fluid contact with a target vessel wall 46. Moreover, the porosity of agent delivery member 18 facilitates a more uniform agent distribution mechanism than is possible with many conventional agent delivery systems since an agent may be evenly absorbed and uniformly expelled by agent delivery member 18.

In one embodiment, the proximal end of delivery member 18 may be functionally shaped, as with a tapered configuration, to facilitate willful retraction of the expanded delivery member 18 back into retention member 34, for example, upon completion of a treatment procedure. It should be appreciated that the distal end of delivery member 18 may also have a tapered configuration to facilitate forward advancement of the delivery member into retention member 34 or into body lumen 46.

One or more end caps 50, 54 may be disposed at the proximal and/or distal ends of agent delivery member 18 to prevent, or at least inhibit, the inadvertent release of therapeutic agent into body lumen 46 through the ends of agent delivery member 18. End caps 50, 54 may be formed from a variety of materials that inhibit or prevent the flow of therapeutic agent therethrough. Thus, the end caps at least partially seal the distal and/or proximal ends of the delivery members. Moreover, end caps 50, 54 may, in the alternative or in addition, inhibit the flow of bodily fluid from body lumen 46 into delivery member 18.

Suitable materials for end caps 50, 54 include, for example, polyisobutylene-styrene block copolymers, silicones, PTFE (fluorinated hydrocarbons), PEBAX, polyurethane, polyethylene, and nylons. End caps 50, 54 may be applied to agent delivery lumen 18 via an adhesive, by thermal melt bonding, by mechanical attachment (e.g., interlocking connectors), or by other application methods known in the art. It should be appreciated that end caps 50, 54 may be formed on delivery member 18 by performing a sealing operation upon the pores of delivery member 18 at the desired surfaces thereof, thereby inhibiting or preventing fluid flow therethrough. Sealing of such pores may occur, for example, with the application of heat or a non-porous material, such as an adhesive, directly to the desired surfaces of delivery member 18.

As illustrated in FIG. 3, agent delivery lumen 26 and guide wire lumen 30 may run co-axially along the length of shaft 22. In such an embodiment, therapeutic agent may flow inside shaft 22 between the inner wall of shaft 22 and the outer wall of wire lumen 30. Further, agent delivery lumen 26 may have an open distal end 58 through which therapeutic agent may be transferred from agent delivery lumen 26 into agent delivery member 18. It should be appreciated that open distal end 58 may occur at the junction 62 between shaft 22 and agent delivery member 18. In an alternative embodiment, agent delivery lumen 26 may extend into the body of agent delivery member 18 such that open distal end 58 occurs at some predetermined location inside agent delivery member 18. Moreover, wire lumen 30 may extend through and beyond the body of agent delivery member 18 to form a distal catheter tip 60, having an opening 30b.

Figure 1A:
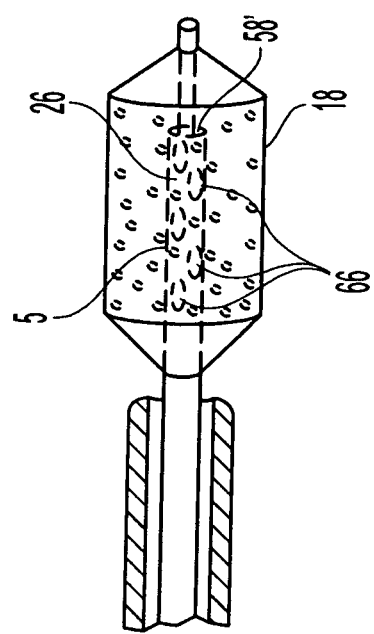
FIG. 1A is an elevational view, partially in cross-section, of an alternative embodiment of a medical device formed in accordance with the present invention.

In a further embodiment, as shown in FIG. 1A, agent delivery lumen 26 may extend into (or completely through) the body of agent delivery member 18 and may have a closed distal end 58'. In such an embodiment, the lumen wall 5 of the agent delivery lumen 26 may have one or more distal delivery openings or ports 66 in contact with the delivery member for distribution of a therapeutic agent within agent delivery member 18. For example, a plurality of distal delivery openings or ports 66 may be disposed in the lumen wall 5 of the agent delivery lumen 26 according to a pre-determined spaced-apart relationship with respect to each other to facilitate uniform distribution of an agent within agent delivery member 18 and, therefore, within body lumen 46. This in combination with the solid cylindrical configuration of agent delivery member 18 provides for a uniform release of the therapeutic agent through the exterior surface of agent delivery member 18 to the tissue wall.

Figure 4:
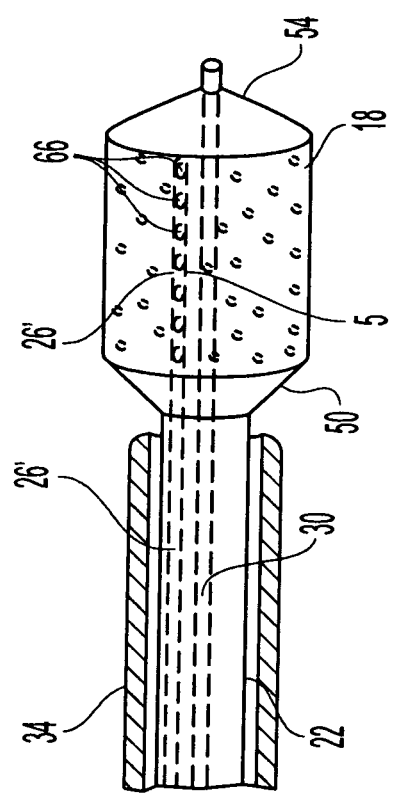
FIG. 4 is an elevational view, partially in cross-section, of an alternative embodiment of a medical device formed in accordance with the present invention.

FIG. 4 illustrates an alternative embodiment of the present invention wherein agent delivery lumen 26' and wire lumen 30 run parallel, but not co-axially, with respect to each other along the length of shaft 22. As in the embodiment of FIG. 3, agent delivery lumen 26' may have an open distal end, which may occur at junction 62, or agent delivery lumen 26' may extend into the body of agent delivery member 18 and have an open distal end that occurs at some predetermined location inside agent delivery member 18. Alternatively, as illustrated in FIG. 4, agent delivery lumen 26' may extend into the body of agent delivery member 18 and may have one or more distal delivery ports 66 in the lumen wall 5 for distribution of a therapeutic agent within agent delivery member 18. For example, a plurality of distal delivery ports 66 may be disposed according to a pre-determined spaced-apart relationship with respect to each other to facilitate uniform distribution of an agent within agent delivery member 18 and, therefore, within body lumen 46.

Figure 5:
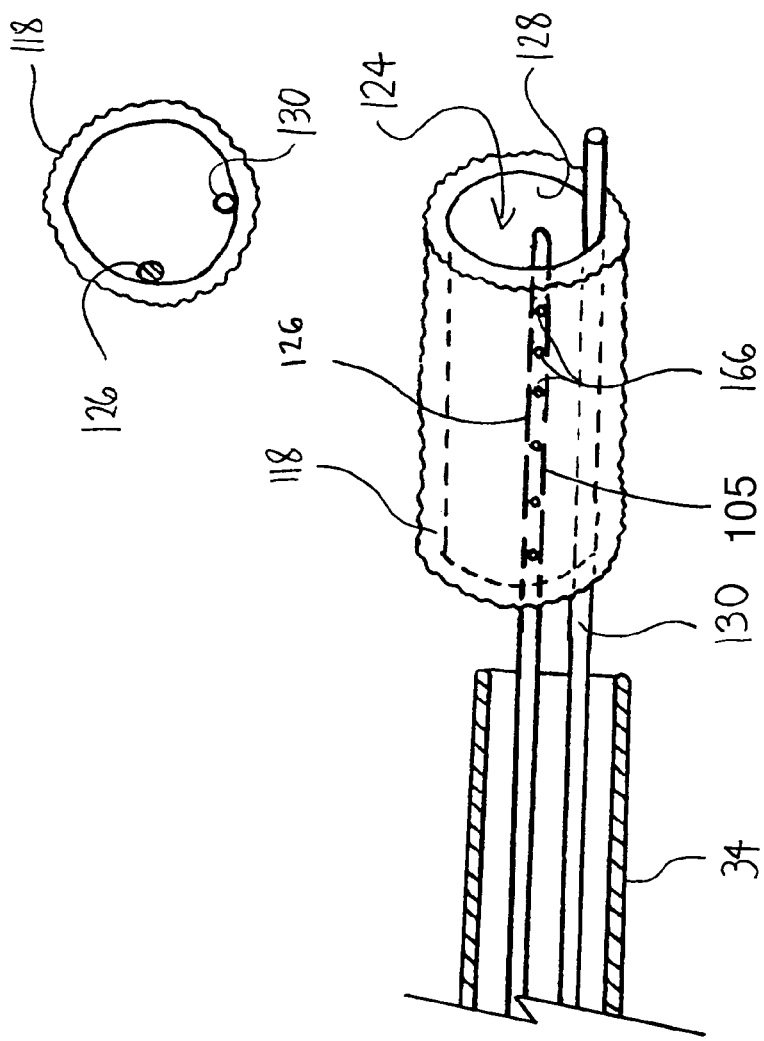
FIG. 5A is an elevational view, partially in cross-section, of a further alternative embodiment of a medical device formed in accordance with the present invention and including a longitudinal conduit.
FIG. 5B is a side elevational view of the medical device shown in FIG. 5A.

FIGS. 5A and 5B illustrate an embodiment of the present invention wherein agent delivery member 118 forms a longitudinal conduit 124 through which bodily fluid may pass. For example, longitudinal conduit 124 may have a generally tubular configuration when expanded to allow blood or other bodily fluids to remain flowing within a target body lumen 46 even while agent delivery member 118 is expanded and operational therein. With such an embodiment, therapeutic procedure times may be extended since regular functioning of the target body lumen 46 is permitted during the procedure. It should be appreciated that longitudinal conduit 124 may be formed by the general shape and configuration of agent delivery member 118 (as illustrated in FIGS. 5A and 5B) or may be formed by an artificial lumen or tube disposed within and extending longitudinally through agent delivery member 118.

In the embodiment of FIGS. 5A and 5B, agent delivery lumen 126 may be attached to the inside surface of delivery member 118 via an attachment means, such as by an adhesive bond or by other attachment means known in the art. It should be appreciated that agent delivery lumen 126 may, alternatively or in addition, be molded within the walls of agent delivery member 118. Wire lumen 130 may be similarly attached to agent delivery member 118 or may, in alternative embodiments, be unattached to agent delivery member 118.

One or more distal delivery ports 166 may be formed in the lumen wall 105 of the agent delivery lumen 126. Such ports 166 may be disposed according to a pre-determined spaced apart relationship with respect to each other and in abutting contact with agent delivery member 118 to facilitate uniform distribution of an agent within agent delivery member 118.

In some embodiments, the inner wall 128 of agent delivery member 118 may be sealed, to inhibit or prevent the inadvertent release of therapeutic agent into body lumen 46 through inner wall 128. Moreover, the sealing may, in the alternative or in addition, inhibit the flow of bodily fluid from body lumen 46 into delivery member 118. It should be appreciated that the distal and/or proximal ends of agent delivery member 118 may also be sealed with distal and/or proximal end caps as described above.

In the embodiment shown in FIG. 1, retention member 34 extends along substantially the entire length of shaft 22. Retention member 34 may have a proximal end 34a accessible to a user for manual operation of retention member 34 and a distal end 34b for selective engagement with agent delivery member 18. Retention member 34 may be, for example, a flexible, thin-walled, longitudinally extending sheath slidably disposed about shaft 22 and configured for movement in the proximal and distal directions with respect to agent delivery member 18. It should be appreciated that retention member 34 may alternatively be configured to extend along a relatively shorter portion of shaft 22, for example at the distal end thereof, and may be operable via one or more rods, wires, or the like accessible from proximal end 10a of device 10.

The components of device 10, such as manifold 14, shaft 22, lumina 26, 30, and retention member 34 may be formed of various materials known in the art, such as various polymers or metals, including but not limited to polycarbonate, ABS, nylon, PEBAX, polyimides, polyamides, or stainless steel.

Figure 6:
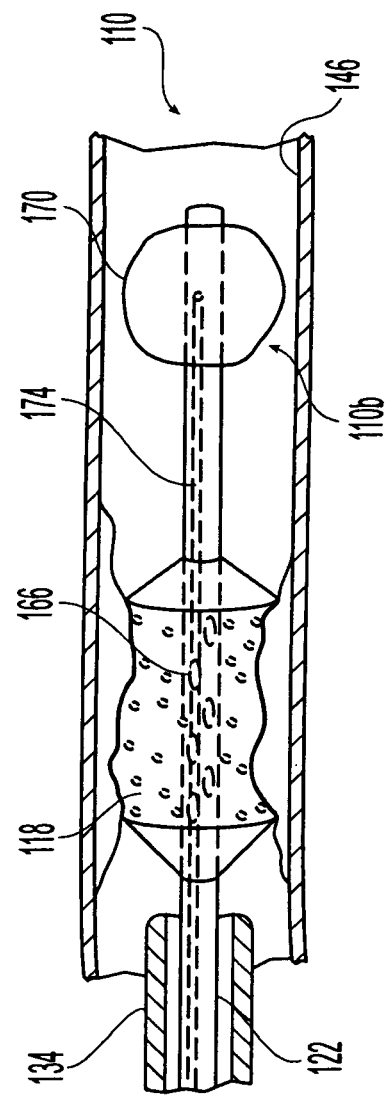
FIG. 6 is an elevational view, partially in cross-section, of an alternative embodiment of a medical device formed in accordance with the present invention and including a balloon.

FIG. 6 illustrates an embodiment of the present invention including an inflatable member, such as balloon 170, operably connected to shaft 122 at distal end 110b of medical device 110. In such an embodiment, a fluid delivery lumen 174 may be provided within shaft 122 for delivering an inflation fluid, such as air, to balloon 170. Further, a fluid delivery port (not shown), for example similar in arrangement to agent delivery port 42 described above, may be provided at a proximal end of medical device 110 for connecting a fluid source to fluid delivery lumen 174 and balloon 170. Balloon 170 may be formed from an expandable material or from a substantially non-expandable material such as polyurethane. In either case, balloon 170 may be inflatable and thus capable of selectively pushing against the inner wall of a body lumen during a procedure.

In operation, medical device 110 may be advanced into a body lumen, such as an arterial vessel 146, until balloon 170 is precisely located at a treatment region, such as a stenotic site. Balloon 170 may then be inflated with a pressurizing fluid provided through fluid delivery lumen 174, thereby dilating the stenotic, plaque-coated treatment region. Once the dilatation action has been completed, the pressurizing fluid may be drained from balloon 170, and medical device 110 may be advanced within arterial vessel 146 beyond the plaque-coated site until balloon 170 is downstream of the site and agent delivery member 118 is precisely located at the site. Then, agent delivery member 118 may be released from retention member 134 (as illustrated in FIG. 6) and operated as described above to deliver a therapeutic agent to the diseased wall of arterial vessel 146. Upon completion of the treatment procedure, medical device 110 may be removed from the body lumen. In some instances, prior to delivery of the therapeutic agent it may be desirable to inflate balloon 170 to distally occlude a body vessel. Delivery of the therapeutic agent is the accomplished through delivery member 118 while the body vessel is occluded by balloon 170. Once delivery of the therapeutic agent is complete, balloon 170 can be deflated and medical device 110 may be removed from the body lumen.

The present invention may be used to deliver and apply a variety of therapeutic agents. As used herein, the term "therapeutic agent" includes, but is not limited to, any therapeutic, such as drugs, and also genetic materials and biological materials. Suitable genetic materials include DNA or RNA, such as, without limitation, DNA/RNA encoding a useful protein, interfering RNA sequences, and DNA/RNA intended to be inserted into a human body including viral vectors and non-viral vectors. Suitable viral vectors include, for example, adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, skeletal myocytes, macrophage), replication competent viruses (e.g., ONYX-015), and hybrid vectors. Suitable non-viral vectors include, for example, artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

Suitable biological materials include, for example, cells, yeasts, bacteria, proteins, peptides, cytokines, and hormones. Examples of suitable peptides and proteins include growth factors (e.g., FGF, FGF-1, FGF-2, VEGF, Endothelial Mitogenic Growth Factors, and epidermal growth factors, transforming growth factor $\alpha$ and $\beta$, platelet derived endothelial growth factor, platelet derived growth factor, tumor necrosis factor $\alpha$, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, and BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include, for example, whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, macrophage, and satellite cells.

The term "therapeutic agent" also includes non-genetic agents, such as: anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, mesalamine, and serine protease inhibitors; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides; vascular cell growth promotors such as growth factors, Vascular Endothelial Growth Factors (FEGF, all types including VEGF-2), growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; tissue inhibitors such as metaloproteinase; cholesterol-lowering agents, vasodilating agents, and agents which interfere with endogenous vasoactive mechanisms; anti-oxidants, such as probucol; antibiotic agents, such as penicillin, cefoxitin, oxacillin, tobranycin; angiogenic substances, such as acidic and basic fibrobrast growth factors, estrogen including estradiol (E2), estriol (E3) and 17-Beta Estradiol; stem cell homing agents, such as stem cell decived factor (SDF); and drugs for heart failure, such as digoxin, beta-blockers, angiotensin-converting enzyme (ACE) inhibitors including captopril and enalopril.

Preferred therapeutic agents include anti-proliferative drugs such as steroids, vitamins, and restenosis-inhibiting agents such as cladribine. Preferred restenosis-inhibiting agents include microtubule stabilizing agents such as Taxol, paclitaxel, paclitaxel analogues, derivatives, and mixtures thereof. For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other preferred therapeutic agents include nitroglycerin, nitrous oxides, antibiotics, aspirins, digitalis, and glycosides.

The amount of the agent delivered through agent delivery member 18 can be adjusted to meet the needs of the patient. In general, the amount of the agent used may vary depending on the application or therapeutic agent selected. One of skill in the art would understand how to adjust the amount of a particular agent to achieve the desired dosage or amount.

In an alternative embodiment of the invention, agent delivery member 18 may be provided in the form of an individual, separate cartridge that is configured to be attached (e.g., snapped) onto device 10 prior to, or during, performance of a therapeutic agent delivery procedure. In such an embodiment, agent delivery member 18 may be loaded with a therapeutic agent prior to, or during, the procedure. Furthermore, in such an embodiment, if agent delivery member 18 is loaded with a therapeutic agent prior to its attachment to device 10, device 10 may be used without agent delivery lumen 126, further simplifying the attachment of agent delivery member 18 to device 10.

In the alternative, or in addition, agent delivery member 18 may be operatively attached to device 10 and may be selectively releasable therefrom. In such an embodiment, agent delivery member 18 may be releasably connected with shaft 22, agent delivery lumen 26, or wire lumen 30 and may be formed from a degradable material such as collagen, polytyrosine polymers, peg-PLGA, polycaprolactone, acellular extra-cellular matrix, fibrin, and chitosan. For example, when device 10 is used for treating peripheral vascular disease ("PVD"), agent delivery member 18 may be delivered to a non-critical vessel, as described above, and released from device 10 to remain in the target area temporarily as a drug reservoir until agent delivery member 18 substantially decomposes.

In the alternative embodiment described above, it is preferable to use an agent delivery member such as agent delivery member 118 of FIGS. 5A and 5B, through which a longitudinal conduit 124 is formed. Agent delivery member 118 may then remain in the target area to act as a drug reservoir without occluding the vessel, thus allowing fluid to continue to flow through the vessel even before delivery member 118 decomposes. Agent delivery member 118 may be releasably connected to shaft 22 and/or agent delivery lumen 126 by hooks that can be actuated to release agent delivery member 118. Many other types of mechanisms and methods for releasably attaching agent delivery member 118 to shaft 22 and agent delivery lumen 126 may also be used. For example, agent delivery member 118 may be attached to shaft 22 and agent delivery lumen 126 by adhesive bonds which are designed to be easily breakable upon a twisting motion of shaft 22 and/or agent delivery lumen 126.

It should be appreciated that the features and components described herein may be used singly or in any combination thereof. Moreover, the present invention is not limited to only the embodiments specifically described herein. The disclosed device 10 may be used with various types of apparatus, including but not limited to over-the-wire catheters; monorail, rapid exchange, or single operator exchange catheters; perfusion catheters; and stent delivery catheters. It should further be appreciated that other applications of the disclosed device 10 in addition to those described herein are also within the scope of the present invention. For example, device 10 may be used to deliver a therapeutic agent to various types of body lumina, including but not limited to the esophagus, urinary tract, and intestines.

While the foregoing description and drawings may represent preferred embodiments of the present invention, it should be understood that various additions, modifications, and substitutions may be made therein without departing from the spirit and scope of the present invention as defined in the accompanying claims. In particular, it will be clear to those skilled in the art that the present invention may be embodied in other specific forms, structures, arrangements, and proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims and not limited to the foregoing description.

What is claimed is:

1. A medical device for delivering a therapeutic agent to an internal portion of a patient's body, the medical device comprising:
    a shaft;
    a self-expanding delivery member in operative communication with the shaft, the delivery member having a proximal end and a distal end and being shaped in a continuous solid cylindrical configuration from a porous material capable of (i) releasing the therapeutic agent to the internal portion of the patient's body and (ii) being in a collapsed state;
    a therapeutic agent delivery lumen defined by a lumen wall, wherein the therapeutic agent delivery lumen is in fluid communication with the delivery member for fluidly connecting the delivery member with a therapeutic agent source;
    a retention member in operative communication with the delivery member, the retention member being configured and arranged to selectively collapse the delivery member; and
    a mechanism capable of applying negative pressure through the therapeutic agent delivery lumen to remove fluid from the delivery member,
    wherein the delivery member expands from a collapsed state to a pre-determined diameter upon retraction of the retention member, and
    wherein the delivery member expands without absorption of a liquid.

2. The medical device of claim 1, wherein the therapeutic agent source is a Luer syringe.

3. The medical device of claim 2, wherein the Luer syringe is the source of the negative pressure.

4. The medical device of claim 2, wherein the delivery member is formed of carboxymethyl cellulose, polyacrylic acid, carboxymethyl starch, chitosan, potassium polymetaphosphates, polyethylene, nylon, polyurethane, PEBAX, silicone, alginate, cotton, polymers cross-linked during phase transition, collagen foams, PLA, PLGA, or PGA.

5. The medical device of claim 1, wherein the porous material is degradable.

6. The medical device of claim 1, wherein the delivery member is shaped from a self-expanding material that is configured and sized to contact at least a portion of a target body lumen when the delivery member is in an expanded state.

7. The medical device of claim 6, wherein the delivery member is configured and sized to self-expand to at least partially conform to the internal contour of the target body lumen when the delivery member is in an expanded state.

8. The medical device of claim 1, further comprising a distal end cap disposed at the distal end of the delivery member, the distal end cap at least partially sealing the distal end of the delivery member.

9. The medical device of claim 1, further comprising a proximal end cap disposed at the proximal end of the delivery member, the proximal end cap at least partially sealing the proximal end of the delivery member.

10. The medical device of claim 1, wherein the proximal end of the delivery member has a tapered configuration when the delivery member is in an expanded condition.

11. The medical device of claim 1, wherein the distal end of the delivery member has a tapered configuration when the delivery member is in an expanded condition.

12. The medical device of claim 1, wherein the delivery member has a length between about 5 mm and about 40 mm.

13. The medical device of claim 1, wherein the shaft has a wire lumen therethrough for receiving a guide wire.

14. The medical device of claim 13, wherein the wire lumen is located within the delivery lumen.

15. The medical device of claim 13, wherein the wire lumen extends into the delivery member.

16. The medical device of claim 1, wherein the mechanism capable of applying negative pressure is a Luer syringe.

* * * * *